(12) United States Patent
Cadell et al.

(10) Patent No.: US 6,700,661 B1
(45) Date of Patent: Mar. 2, 2004

(54) METHOD OF OPTIMIZING WAVELENGTH CALIBRATION

(75) Inventors: Theodore E Cadell, Conestogo (CA); Geng Lu, Waterloo (CA)

(73) Assignee: CME Telemetrix, Inc., Ontario (CA)

( * ) Notice: Subject to any disclaimer, the term of this patent is extended or adjusted under 35 U.S.C. 154(b) by 88 days.

(21) Appl. No.: 10/110,539

(22) PCT Filed: Oct. 13, 2000

(86) PCT No.: PCT/CA00/01182

§ 371 (c)(1),
(2), (4) Date: Apr. 15, 2002

(87) PCT Pub. No.: WO01/27572

PCT Pub. Date: Apr. 19, 2001

Related U.S. Application Data (60) Provisional application No. 60/159,428, filed on Oct. 14, 1999.

(51) Int. Cl.$^7$ .................................................. G01J 3/28
(52) U.S. Cl. ......................... 356/326; 702/85; 250/252.1
(58) Field of Search .................................. 356/300, 326, 356/328, 334; 702/85; 250/252.1

(56) References Cited

U.S. PATENT DOCUMENTS

| | | |
|---|---|---|
| 5,361,758 A | 11/1994 | Hall et al. |
| 5,771,094 A | 6/1998 | Carter et al. |
| 6,415,233 B1 * | 7/2002 | Haaland ..................... 702/22 |

FOREIGN PATENT DOCUMENTS

| | | | |
|---|---|---|---|
| WO | WO 94/08225 | * | 4/1994 |

* cited by examiner

*Primary Examiner*—F. L. Evans
(74) *Attorney, Agent, or Firm*—Sughrue Mion, PLLC

(57) ABSTRACT

The present invention provides a method of calibrating the wavelength of a target instrument, based on a calibration model developed for a primary instrument. The method comprises: (a) obtaining a reference set of at least two wavelength calibration parameters for the primary instrument; (b) obtaining a target set of at least two corresponding wavelength calibration parameters for the target instrument; (c) measuring a reference spectral response of a sample with the primary instrument; (d) measuring a target spectral response of the sample with the target instrument; (e) iteratively adjusting the target set of wavelength calibration parameters; (f) for each target set of wavelength calibration parameters, determining spectral residuals corresponding to that target set; and (g) selecting an optimum set of wavelength calibration parameters based on the spectral residuals for each target set of wavelength calibration parameters.

20 Claims, 5 Drawing Sheets

METHOD OF OPTIMIZING WAVELENGTH CALIBRATION

This is a National stage entry under 35 U.S.C. §371 of Application No. PCT/CA00/01182 filed Oct. 13, 2000, which claims benefit of Provisional Application No. 60/159,428 filed Oct. 14, 1999; the above noted prior applications are all hereby incorporated by reference.

FIELD OF THE INVENTION

The present invention relates generally to the fields of spectroscopy and of calibrating a spectroscopic device, such as a spectrometer for predicting analyte levels. More particularly, the present invention relates to a method of optimizing wavelength calibration to facilitate the transfer of a calibration model from a primary device to a secondary device.

BACKGROUND OF THE INVENTION

Spectroscopy is based on the analysis of how incident radiation interacts with the vibrational and rotational states of molecules, often within a matrix such as blood or living tissue, which are of analytical interest. Spectrometers and other similar devices that use spectroscopic measurement techniques have gained increased popularity because of the ability to provide fast and non-invasive measurements of concentrations of different chemicals or analytes. In particular, spectrophotometry is a type of spectroscopy commonly used to quantitatively measure properties such as analyte concentration(s) based on spectral energy distribution in the absorption spectrum of a sample solution or medium. In spectrophotometry, the energy distribution is typically analyzed within a range of the visible, ultraviolet, infrared, or near-infrared spectra. For example, near-infrared radiation (NIR) is electromagnetic radiation having a wavelength between about 750 and 2500 nanometers (nm). Near-infrared spectrophotometry generally uses instruments with quartz prisms in monochromators and with lead sulfide photoconductor cells or photodiodes as detectors to observe absorption bands. Near-infrared spectrophotometry is, for example, increasingly being used to measure in vivo analytes such as glucose, fructose, glycerol, and ethanol.

Spectroscopic devices are well known in the art and are described in detail, for instance, in U.S. Pat. Nos. 5,361,758 and 5,771,094, the contents of which are incorporated herein by virtue of this reference. In general, a typical spectrometer system includes a light source which is projected through the sample to be examined, a sample interface mechanism, a spectrometer to separate the light into its component wavelengths, a detector, amplification electronics, and a microprocessor or computer system. By measuring the loss (absorption), between the source and the detector and applying appropriate chemometric or mathematical techniques, it is possible to determine the chemical analytes being examined since different chemicals absorb different amounts of light. The detector or photodetector generally includes a photodiode array of pixels enabling the detector to simultaneously detect the intensities of a number of different spectral components at distinct wavelengths. The intensities at these distinct wavelengths can be used to predict, in turn, the quantities or concentrations of the analyte(s) of interest.

Calibration of spectrometers and of analytical instruments in general is necessary to ensure the accuracy of measurements performed by such devices. In essence, calibration is the development of a model or algorithm that predicts the properties (e.g. analyte concentrations) of a sample from the spectrometer's response. To calibrate a spectrometer, the spectral response of several calibration samples or standards having known concentrations of an analyte of interest is measured. By combining the known concentration data with the measured spectral response data, a calibration model (i.e. a mathematical relationship) can be developed using a "best fit" regression technique (e.g. partial least squares or PLS) between the spectral measurements and analyte or property of interest. The calibration model or algorithm is then stored in a non-volatile memory, such as for example, in a microprocessor system of the device. In most cases, the spectrometer's response is a measure of a number of variables, e.g. a number of different chemical species present in a sample, and so calibration is based on a multivariate calibration model. The spectrometer and its calibration model can then be used to estimate the property or properties (e.g. analyte concentrations) of an unknown sample. By detecting the pixel position of a spectral component measured by the spectrometer, the wavelength of that spectral component is known, and consequently a prediction can be calculated by the microprocessor using the calibration algorithm.

Calibration, i.e. the development and calculation of a calibration algorithm, is generally performed on a primary instrument or device when it is initialized or installed or when any of its components are replaced. This primary instrument is often a member of a group of similar instruments produced by the same manufacturer, and having the same component types, model number, and so on. The other members of this instrument group are hereinafter referred to as "secondary" or "target" instruments. Because calibration is a lengthy and involved process, it is often not practical to individually recalibrate each secondary instrument in a set since this may require, among other difficulties, a large number of calibration samples at the site of each secondary instrument. Instead, for many spectroscopic applications, the calibration model developed for the primary instrument is transferred to each secondary instrument. For example, the transfer of calibration algorithms between primary and secondary instruments is often desirable with NIR spectrophotometers.

However, when a calibration model determined using measurements on a primary instrument is transferred to another instrument of the same type, a loss of accuracy generally occurs. This loss of accuracy is due to the innate differences that exist between any two physical devices, resulting in a variation in spectral responses (i.e. the correlation between pixel locations and wavelength) and affecting the reproducibility of measurements with the secondary device.

Wavelength calibration is performed to reduce the inaccuracy inherent in calibration algorithm transfer between instruments. For this purpose, calibration light source(s) having spectral lines at two or more known wavelengths are typically used to provide wavelength calibration parameters. A calibration light source may be a laser or a mercury lamp, for example. The pixel locations of the spectral lines of the calibration light source are more accurately fitted to the known wavelengths to improve the calibration reference. The calibration model or algorithm can then be adjusted to assign a more accurate wavelength value to each pixel of the multi-pixel detector array.

However, when using a calibration light source such as a laser to locate a selected wavelength on the pixel array of a spectrometer, wavelength calibration to within ±0.2 nm is typically very difficult to achieve, and more accurate wavelength calibration is generally not possible. For many spectroscopic applications, this level of wavelength inaccuracy remains unacceptable, since it can introduce significant errors in analyte concentration predictions or estimations, particularly for measurements performed within complex media such as living issue or blood.

Similarly, it may also be desirable to transfer a calibration developed for a primary instrument to a target instrument, where the target instrument is the primary instrument after a period of time has elapsed. During that time, the primary instrument's response may have changed due to detector instability, temperature variations, drift in the electronics of the primary instrument, or other causes. Consequently, the primary instrument may require subsequent wavelength recalibration to avoid significant inaccuracies.

Thus, wavelength calibration of a pixel (e.g. photodiode) array spectrometer and adjustment of the calibration model to minimize differences between instruments is highly desirable, and there is a need for an improved method of wavelength calibration to facilitate and improve the transfer of a calibration algorithm or model from a primary instrument to a secondary instrument (which may include the primary instrument at a later time). The ability to accurately transfer calibration algorithms from a primary device to a secondary device is especially desirable in the case of NIR spectrophotometers, for example.

SUMMARY OF THE INVENTION

The present inventors have developed a method in order to provide an improved and more accurate method of wavelength calibration to facilitate transfer of a calibration algorithm or model from a primary instrument to a secondary or target instrument (including to the primary instrument at a later time).

In one aspect, the present invention provides a method of calibrating the wavelength of a target instrument, said target instrument being provided with a calibration model developed for a primary instrument, the method comprising:

(a) obtaining a reference set of at least two wavelength calibration parameters for the primary instrument;

(b) obtaining a target set of at least two corresponding wavelength calibration parameters for the target instrument;

(c) measuring a reference spectral response of a sample with the primary instrument;

(d) measuring a target spectral response of said sample with the target instrument;

(e) iteratively adjusting the target set of wavelength calibration parameters;

(f) for each target set of wavelength calibration parameters, determining spectral residuals corresponding to that target set; and (g) selecting an optimum set of wavelength calibration parameters based on the spectral residuals for each target set of wavelength calibration parameters.

Preferably, step (c) comprises measuring wavelengths of the reference spectral response on a reference detector in said primary instrument and step (d) comprises measuring wavelengths of the target spectral response on a target detector in said target instrument.

More preferably, each of said reference detector and said target detector is a photodiode array detector, and each of said photodiode array detectors comprises a plurality of pixels for detecting said wavelengths.

In an embodiment, step (a) comprises generating a reference wavetable from the reference set of wavelength calibration parameters for the primary instrument, and step (b) comprises generating an initial target wavetable from the target set of wavelength calibration parameters for the target instrument, each of said wavetables providing a correlation between the pixel locations and the corresponding wavelengths in each respective instrument.

The method may further comprise: interpolating the target spectral response measured by the target instrument on to the reference wavetable; and measuring a spectral difference between the target spectral response and the reference spectral response.

The method may further comprise: interpolating the spectral difference back to the target wavetable; and subtracting the spectral difference from the initial target spectral response, so as to provide a photometrically corrected target spectral response.

The method may further comprise: interpolating the photometrically corrected target spectral response from the initial target wavetable to the reference wavetable to provide a corrected set of measured spectral data for the target instrument.

In an alternative embodiment, the method may further comprise: interpolating both the target spectral response measured by the target instrument and the reference spectral response measured by the reference instrument on to a selected wavetable; and measuring a spectral difference between the target spectral response and the reference spectral response in said selected wavetable.

This alternative method may further comprise: interpolating both the spectral difference and the initial target spectral response on to a selected wavetable; and subtracting the spectral difference from the initial target spectral response, so as to provide a photometrically corrected target spectral response.

This alternative method may further comprise: interpolating both the photometrically corrected target spectral response and the reference spectral response from the reference table on to a selected wavetable, so as to provide a corrected set of measured spectral data for the target instrument.

In each method, providing a corrected set of measured spectral data for the target instrument is repeated for each iterative adjustment in step (e).

Preferably, the iterative adjustment in step (e) comprises step-wise adjusting the pixel locations of the target detector in predetermined steps.

More preferably, step (g) comprises minimizing a parameter representative of spectral residuals of the target instrument, the spectral residuals being the difference between the corrected set of measured spectral data and an estimated set of spectral data for the target instrument.

More preferably, the parameter representative of the spectral residuals is the sum of the absolute values of all residual components across a spectrum of interest.

More preferably, the spectral residuals are calculated, during each iteration, using one of principle components regression, principal components analysis, and partial least squares.

In an alternative embodiment, the parameter representative of the spectral residuals is one of the mean, median, and root mean square of the absolute values of at least some residual components.

Preferably, the spectral residuals are calculated, during each iteration, using one of principle components regression, principal components analysis, and partial least squares.

More preferably, said iterative adjustment in step (e) comprises step-wise adjusting the pixel locations of the target detector in predetermined steps.

In another aspect, the present invention provides a method of recalibrating the wavelength of a target instrument, said target instrument being provided with a calibration model developed for a primary instrument, the method comprising:

(a) obtaining a reference set of at least two wavelength calibration parameters for the primary instrument, (b) obtaining a target set of at least two corresponding wavelength calibration parameters for the target instrument;

(c) measuring a reference spectral response of a sample with the primary instrument;

(d) measuring a target spectral response of said sample with the target instrument;

(e) iteratively adjusting the target set of wavelength calibration parameters;

(f) for each target set of wavelength calibration parameters, determining spectral residuals corresponding to that target set; and (g) selecting an optimum set of wavelength calibration parameters based on the spectral residuals for each target set of wavelength calibration parameters.

In a preferred embodiment, steps (b) and (d) occur after steps (a) and (c), and the target instrument to be recalibrated is the primary instrument itself.

The objects and advantages of the present invention will be better understood and more readily apparent with reference to the remainder of the description in conjunction with the accompanying drawings.

BRIEF DESCRIPTION OF THE DRAWINGS

For a better understanding of the present invention and to show more clearly how it may be carried into effect reference is made to the remainder of the description and the attached drawings which illustrate, by way of example, a preferred embodiment of the invention.

DETAILED DESCRIPTION OF THE INVENTION

For convenience, the following description assumes that a calibration model has been developed, in known manner, for predicting a desired property or properties based on measurements performed by a primary spectroscopic instrument, such as a NIR photodiode array spectrophotometer for measuring blood glucose concentration levels. In most spectroscopic applications, the calibration model will be multivariate, i.e. it will depend on a plurality of parameters or components. The number of pixels in the detector of such a device is typically a power of two, e.g. 256, 512, or 1024.

Figure 1:
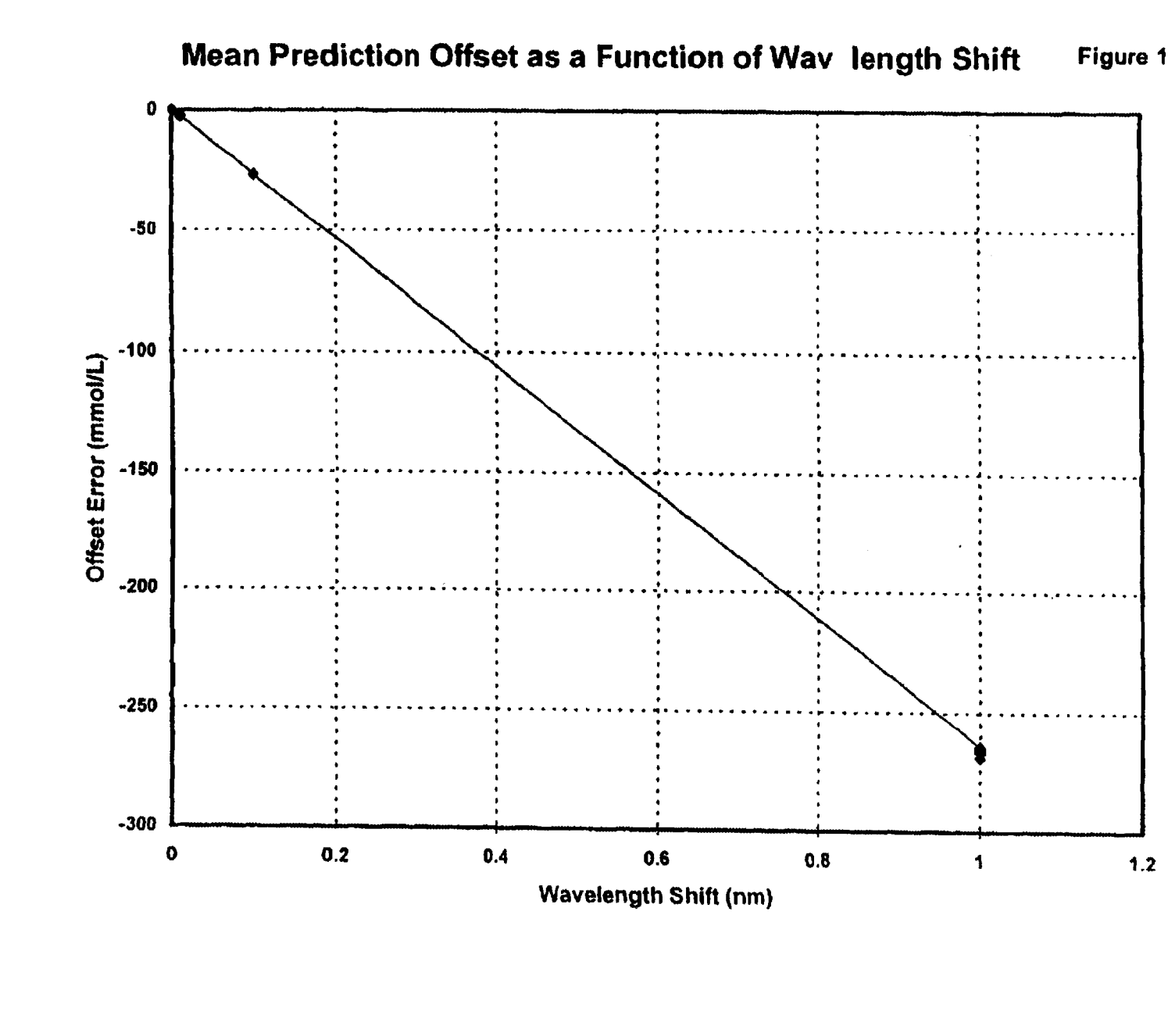
FIG. 1 illustrates the offset of secondary instrument predictions as a function of wavelength shift.
Figure 2:
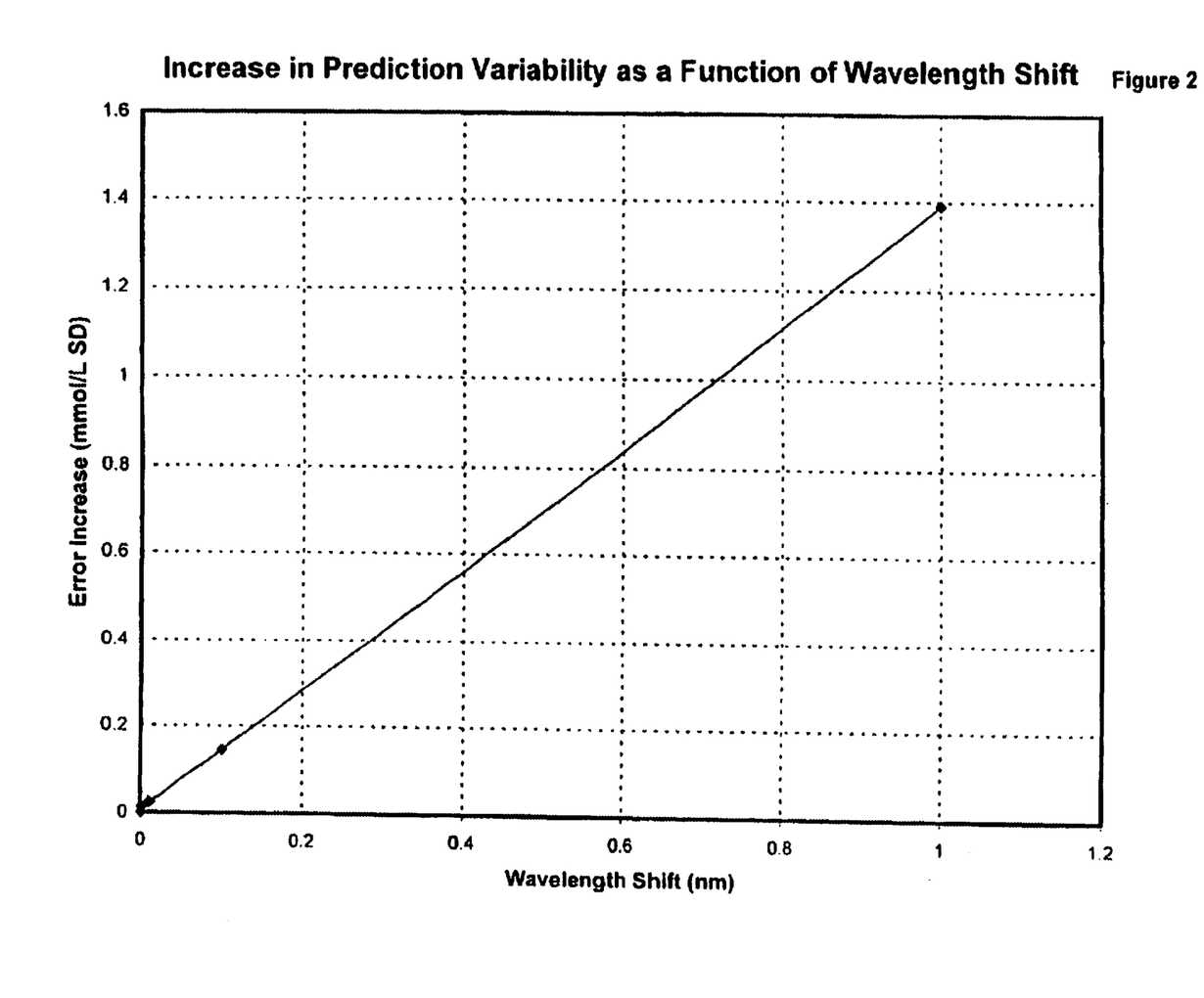
FIG. 2 illustrates the amount of prediction variability (random errors) as a function of wavelength shift.

If the calibration model is transferred for use with a secondary or target instrument of the same type as the primary instrument, any wavelength shift between the spectral response (ie. a shift in pixel location with respect to wavelengths) of the secondary instrument compared to the primary instrument will decrease the accuracy and reproducibility of predictions based on measurements with the secondary instrument. Specifically, as this wavelength shift between primary and secondary instruments increases, the secondary instrument predictions will be increasingly offset, as illustrated in FIG. 1, and will also exhibit an increase in the amount of prediction variability (random errors), as illustrated in FIG. 2. These ill effects generally are even more pronounced and severe as the complexity of the multivariate calibration model increases.

The present invention provides a method of calibrating the wavelength of the secondary instrument or device to improve the accuracy and reproducibility of the predictions based on measurements by the target or secondary instrument and the transferred calibration algorithm. As mentioned above, the target device can also be the primary device, a period of time after the primary device was originally calibrated. In doing so, the wavelength calibration method of the present invention reduces both the offset and the prediction variability in the secondary or target device predictions to within much more acceptable levels.

The present invention is based, in part, on the realization that once a calibration algorithm is determined for a primary instrument, prediction of measurements on the secondary instruments using this algorithm affects the magnitude of spectral residuals. According to a preferred embodiment of the present invention, the method may be carried out as follows.

Initially, two or more wavelength calibration parameters $P_{n1}$, $P_{n2}$, ... $P_{nN}$ are separately obtained for each of the primary and the secondary instruments. Preferably, the wavelength calibration parameters for the primary instrument are determined contemporaneously with or at approximately the same time as generation of the calibration model therefor. These parameters are obtained by using wavelength calibration radiation sources of known wavelengths with each instrument and determining the pixel location corresponding to the known wavelength of each source used. In general, at least two sources, and two wavelength calibration parameters, are required for the purposes of the present invention For example, for a NIR photodiode array spectrophotometer having a 256 pixel array and operable to provide a spectral response between about 600 nm and 1100 nm, first and second laser wavelength calibration sources having wavelengths of 632 nm and 1064 nm respectively could be used. The pixel locations corresponding to the laser sources are then recorded for each of the primary and the secondary instruments to provide the wavelength calibration parameters ($P_{n1}$ and $P_{n2}$). As discusd above, such laser sources are generally only capable, at best, of an accuracy of about 0.2 nm. Consequently, it is often likely that the initial wavelength calibration parameters obtained for the secondary instrument will not provide sufficient accuracy for many spectroscopic applications.

From the wavelength calibration parameters $P_{n1}$, $P_{n2}$, ... $P_{nN}$ a primary or reference wavetable is generated for the primary device and an initial secondary wavetable is generated for the secondary device. The wavetables essentially provide the correlation between the pixel locations of the specific device and wavelength. The wavetables may be generated by a number of possible analytical fitting techniques including linear and trigonometric methods. For example, in a linear fit one pixel maps to a constant wavelength difference, e.g. 2 nm/pixel.

The spectral responses or spectra measured by each instrument for a typical or representative sample are collected next. The set of measured spectral components provided by the reference (primary) and secondary instruments are hereinafter referred to as $S_{ref}$ and $S_{sec}$ respectively. The particular choice of sample used for these measurements is not key. For example, for blood analyte measurements a Finger Phantom® available from Non in Medical, Inc. can optionally be used.

The spectra measured by the secondary instrument $S_{sec}$ is then interpolated from the initial secondary wavetable to the reference wavetable. In other words, the spectral components measured by the secondary instrument are interpolated on to the reference wavetable, so that the secondary spectral components correspond to the reference pixel locations. In effect, the secondary spectral components provide the secondary pixel locations; the secondary pixel locations are interpolated to specific wavelengths, as provided by the secondary wavetable; and those wavelengths are (inversely) interpolated to reference pixel locations, as provided by the reference wavetable. This interpolation may be based on any one of a number of possible interpolation techniques such a linear interpolation, trigonometric interpolation, and Savitsky-Golay smoothed derivative techniques. Whichever wavetable generation technique is chosen, that technique is preferably used consistently throughout other interpolation steps in the present invention.

The difference between the secondary spectral components (as they correspond to the reference pixel locations) and the primary or reference spectral components $S_{ref}$ is taken next. This spectral difference is then interpolated back to the secondary wavetable—in reverse manner to the interpolation just described above—to provide a spectral difference $S_{dif}$ corresponding to the secondary wavetable. By subtracting the spectral difference $S_{dif}$ from the initial secondary spectral components $S_{sec}$ (which remain correlated to the secondary wavetable), a photometric correction for the secondary measurements is provided. The above provides a relatively coarse correction, however this is nonetheless sufficient, for the purposes of the present invention, to adequately compensate for physical differences between the primary and secondary instruments, such as differences in the instruments' photodiode detectors. As a result, the spectral difference $S_{dif}$ need not be recalculated during the iterative steps of the present invention.

The photometrically corrected secondary spectral measurements ($S_{sec}-S_{dif}$) are then interpolated from the initial secondary wavetable to the reference wavetable (similar to as was done above for the raw secondary spectral measurements) to provide a corrected set of measured spectral data $S^*_{sec}$ for the secondary instrument that is suitable for subsequent comparison and analysis, as described below.

In accordance with the present invention, the wavelength calibration parameters $P_{n1}$, $P_{n2}$, ... $P_{nN}$ (i.e. the pixel positions corresponding to the calibration source wavelengths) for the secondary instrument are iteratively adjusted until an optimum set of wavelength calibration parameters (and corresponding wavetable) is arrived at. For each distinct set of wavelength calibration parameters $P_{n1}$, $P_{n2}$, ... $P_{nN}$, the secondary wavetable is regenerated and the corrected set of measured spectral data $S^*_{sec}$ for the secondary instrument is adjusted.

Determination of the optimal set of wavelength calibration parameters is found by minimizing a parameter representative of the spectral residuals of the secondary instrument (which varies with each set of wavelength calibration parameters). The spectral residuals are defined as the difference between the corrected set of measured spectral data $S^*_{sec}$ and an estimated set of spectral data $X_{sec}$ for the secondary instrument. Preferably, the parameter used to assess the spectral residuals is the sum of the absolute values of all residual components across a spectrum of interest. Alternatively other parameters representative of the overall spectral residuals could be used such as the mean, median, or root mean square of the absolute values of some or all residual components. The sum of the spectral residuals is preferably calculated using the full range of the instrument spectrum, where accurate calibration is desired and measurements are sensitive over the entire instrument range. Also, if the end (or other) regions of the spectrums are overly noisy, it may be desirable to exclude these regions from spectral residual consideration. Generally, however, any spectral region of interest can be chosen for spectral residual evaluation and consideration.

The spectral residuals can be calculated, during each iteration, using several possible factor analysis or multivariate regression techniques. These include principal components regression (PCR), principle components analysis (PCA), and partial least squares (PLS).

According to a preferred embodiment of the present invention, principal components analysis (PCA) is used to calculate the spectral residuals. Principal components analysis (PCA) is a well known method commonly used to reduce the dimensionality of a matrix of measured data, simplifying computations while preserving as much as of the original data information as possible. For example, a spectral component matrix S of order i×j can have a PCA decomposition $$S_{i \times j} = T_{i \times k} P_{j \times k}^T + E_{i \times j}$$

where T is the PCA scores matrix, $P^T$ (of dimension k×j) is the transformed PCA loadings matrix P, and E is the residuals matrix. The scores matrix T provides information about the spectral patterns in the measurement data, whereas the loadings matrix P reflects the influence of each of the various parameters in the spectral patterns. The matrix product $T P^T$ effectively provides an estimate of the spectral response, with the difference between the measured response S and the estimated response $T P^T$ being the spectral residuals matrix E (containing the individual spectral residual components). As will be understood by those skilled in the art, the dimension k represents the number of principal components used in the decomposition and is a matter of computational choice. The principal components are created in order of decreasing variance, i.e. the first principal component accounts for the most variance in the data, the second principal component accounts for the next greatest amount of variance in the data, and so on. It should also be noted that because the PCA is an orthogonal transform (i.e. it provides an orthogonal basis), $P P^T = I$, the identity matrix.

The following steps may be followed to calculate, using PCA techniques, the spectral residuals matrix E for a specific set of wavelength calibration parameters. First, a PCA decomposition is performed on the spectra measured by the reference instrument (for example with k=7, i.e. seven principal components). This provides a PCA reference scores matrix, $T_{ref}$, and a PCA loadings matrix, $P_{ref}$. Next, the corrected set of measured spectral data for the secondary instrument, $S^*_{sec}$, can be transformed or injected into the PCA space of reduced dimensionality to provide a secondary scores matrix, $T_{sec}$, as follows:

$$T_{sec} = S^*_{sec} P_{ref}$$

so that the estimated set of spectral data for the secondary instrument $X_{sec}$ is given as $$X_{sec} = T_{sec} P_{ref}^T$$

and therefore, the spectral residuals $E_{sec}$ of the secondary spectral data are given as $$E_{sec} = S^*_{sec} - X_{sec} = S^*_{sec} - T_{sec} P_{ref}^T$$

Figure 3:
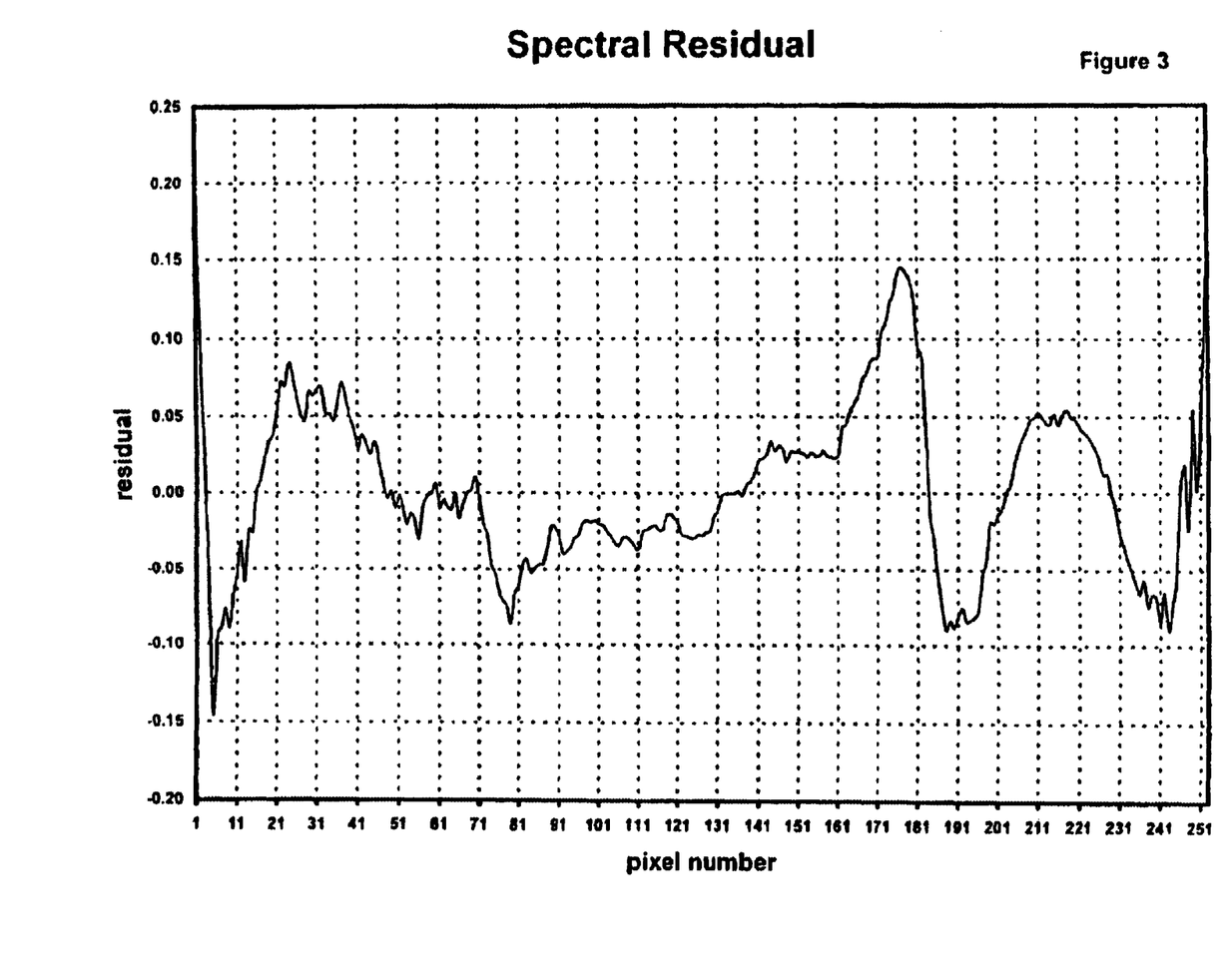
FIG. 3 shows an exemplary plot of the spectral residuals for a NIR photodiode array spectrophotometer having a 256 pixel array.

FIG. 3 shows an exemplary plot of the spectral residuals for a NIR photodiode array spectrophotometer having a 256 pixel array and operable to provide a spectral response between about 600 nm and 1100 nm.

Thus, for each distinct set of wavelength calibration parameters $P_{n1}$, $P_{n2}$, ... $P_{nN}$ a secondary wavetable is calculated as described above. As indicated above, it is not necessary to recalculate the difference matrix $S_{dif}$ nor the photometrically corrected secondary spectral measurements $(S_{sec} - S_{dif})$ for each distinct set of wavelength calibration parameters. Indeed, this is preferably not done for simplicity. However, the interpolation of the photometrically corrected secondary spectral measurements from the recalculated secondary wavetable to the reference wavetable (which does not change) is re-performed with each iteration or change in wavelength calibration parameters. Thus, the corrected set of measured spectral data for the secondary instrument, $S^*_{sec}$, is adjusted with each iteration, despite the fact that the photometric correction is preferably not re-performed.

From the recalculated or adjusted $S^*_{sec}$ matrix, the corresponding spectral residuals matrix $E_{sec}$ of the secondary spectral data is then determined in the above-described manner. As mentioned, determination of the optimal set of wavelength calibration parameters is found by minimizing a parameter representative of the spectral residuals $E_{sec}$ of the secondary instrument. Preferably, the absolute values of some or all of the residual components in the spectral residuals matrix $E_{sec}$ are summed, and the summed value provides the parameter to be minimized during iterations. Alternatively, other parameters representative of the overall spectral residuals could be used such as the mean, median, or root mean square of the absolute values of all residual components.

It is desirable to use all or most of the residual components in the spectral residuals matrix $E_{sec}$ for the absolute value calculation when the full range of the spectral instruments is of interest (i.e. measurements are sensitive to all parts of the available spectrum). Furthermore, if some small spectral regions (e.g. the upper and lower limits of the instrment's spectrum) are adversely affected by noise, it may be desirable to exclude these regions from spectral residual consideration. Generally, however, any spectral region of interest can be chosen for spectral residual evaluation and consideration. In such a case, only the components in the spectral residuals matrix $E_{sec}$ corresponding to those regions are assessed (e.g. only the absolute value of those components are summed).

During the step-wise iterative adjustments, the pixel locations corresponding to the wavelength calibration parameters $P_{n1}$ and $P_{n2}$ can be individually step-wise adjusted in any suitably-sized steps. For instance, adjustment by 0.02 pixels per step can provide greatly improved wavelength calibration.

Figure 4:
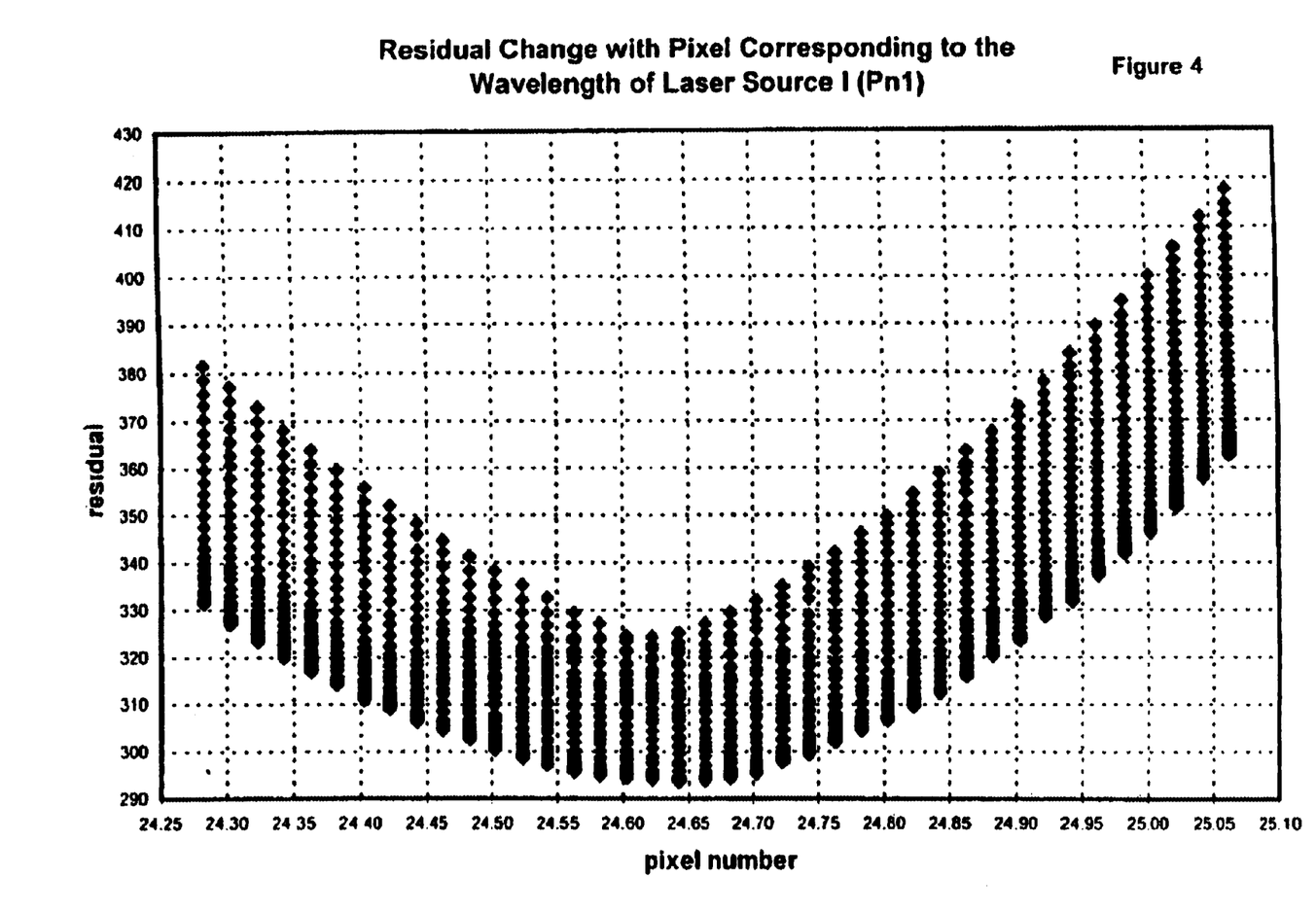
FIG. 4 graphically illustrates the change in the sum of the absolute value of spectral residual components for a first wavelength calibration parameter.
Figure 5:
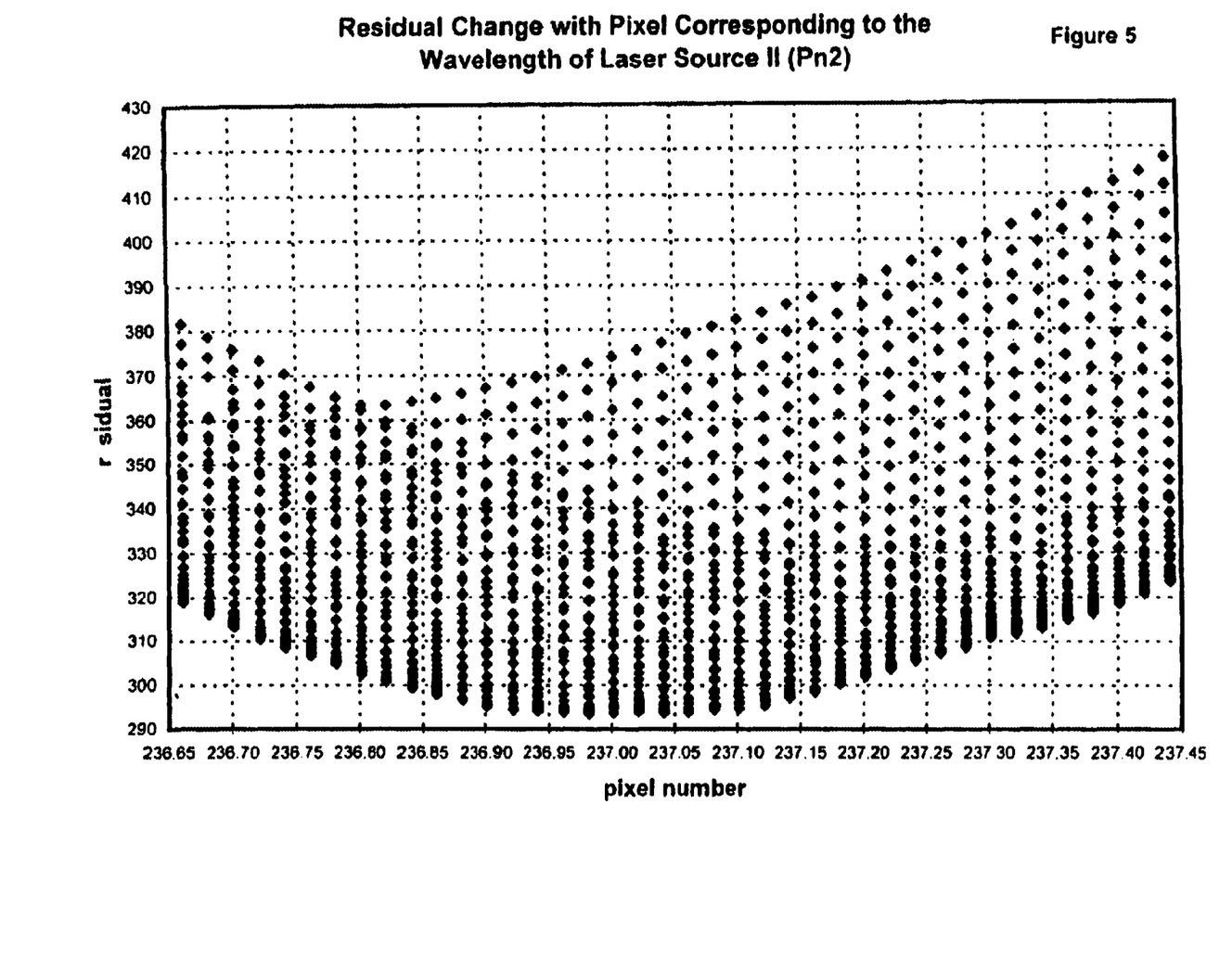
FIG. 5 graphically illustrates the change in the sum of the absolute value of spectral residual components for a second wavelength calibration parameter.

Preferably, only two wavelength calibration parameters $P_{n1}$ and $P_{n2}$ are used so that computational complexity is kept to a minimum. FIGS. 4 and 5 illustrate the application of the method of the present invention to a calibration model transfer between NIR photodiode array spectrophotometers having a 256 pixel array and operable to provide a spectral response between about 600 nm and 1100 nm. The laser source 1 referred to in FIG. 4 and the laser source 2 referred to in FIG. 5 may have wavelengths of 632 nm and 1064 nm respectively. Each of these Figures graphically illustrates the change in the sum of the absolute value of spectral residual components for the specific wavelength calibration parameter. As shown in FIG. 4, the minimum for $P_{n1}$ corresponding to laser source 1 is approximately at 24.64 pixels. Similarly, as shown in FIG. 5, the minimum for $P_{n2}$ corresponding to laser source 2 is approximately at 236.98 pixels.

It will be apparent to those skilled in the art that the simultaneous minimization of spectral residuals for two wavelength calibration parameters $P_{n1}$ and $P_{n2}$ is effectively a two dimensional minimization problem (i.e. finding a minimum on a two dimensional surface). As the number of wavelength calibration parameters grows to N, the minimization becomes an N-dimensional task and accordingly more complex. In addition, the inventors have found that to avoid the possibility of inadvertently focusing or converging on a local spectral residual minimum, it is preferable to adjust each of the wavelength calibration parameters relatively successively, and not to repeatedly vary a single wavelength calibration parameter over many iterations while maintaining the other wavelength calibration parameter(s) constant throughout. As will be appreciated by those skilled in the art, the method of the present invention can be effectively carried out with the aid of a suitably programmed microprocessor system.

Thus, the present invention provides a more accurate determination of the pixel locations of the calibration wavelengths located on the secondary or target instrument. The inventors have found that the iterative wavelength calibration method of the present invention can provide accuracy that is an order of magnitude better than wavelength calibration using laser calibration sources alone (as is typically done in the prior art).

While preferred embodiments of the present invention have been described, the embodiments disclosed are illustrative and not restrictive.

For example, while reference has been made above to interpolating various spectral responses to one of the reference wavetable and the target wavetable, it will be understood by those skilled in the art that a wavetable can be artificially generated and that both the reference spectral response and the initial target spectral response may be interpolated to the same artificially generated wavetable to measure a spectral difference between them. Furthermore, it will be understood that both this spectral difference and the initial target response may be interpolated to the same artificially generated wavetable or another artificially generated wavetable, and the spectral difference may be subtracted from the initial target spectral response, so as to provide a photometrically corrected target spectral response. Finally, it will be understood that this photometrically corrected target spectral response and the reference spectral response may be interpolated on to one of the artificially generated wavetables or yet another artificially generated wavetable to provide a corrected set of measured spectral data for the target instrument.

Furthermore, it will be appreciated by those skilled in the art that the method according to the present invention can be used to recalibrate the primary instrument itself, where a reference set of wavelength calibration parameters has been previously obtained for the primary instrument (i.e. the "target" instrument is the primary instrument in this case). This assumes that the sample used to obtain the reference set of wavelength calibration parameters is stable for the recaliration procedure after the passage of time, or that the sample can be accurately reproduced in a controlled manner. Thus, the sample used for calibration may be a synthetic rather than a patient sample which may become unstable over a relatively short period of time.

We claim:

1. A method of calibrating the wavelength of a target instrument, said target instrument being provided with a calibration model developed for a primary instrument, the method comprising:

(a) obtaining a reference set of at least two wavelength calibration parameters for the primary instrument;

(b) obtaining a target set of at least two corresponding wavelength calibration parameters for the target instrument;

(c) measuring a reference spectral response of a sample with the primary instrument;

(d) measuring a target spectral response of said sample with the target instrument;

(e) iteratively adjusting the target set of wavelength calibration parameters;

(f) for each target set of wavelength calibration parameters, determining spectral residuals corresponding to that target set; and (g) selecting an optimum set of wavelength calibration parameters based on the spectral residuals for each target set of wavelength calibration parameters.

2. A method according to claim 1, wherein step (c) comprises measuring wavelengths of the reference spectral response on a reference detector in said primary instrument and step (d) comprises measuring wavelengths of the target spectral response on a target detector in said target instrument.

3. A method according to claim 2, wherein each of said reference detector and said target detector is a photodiode array detector, and each of said photodiode array detectors comprise a plurality of pixels for detecting said wavelengths.

4. A method according to claims 3, wherein step (a) comprises generating a reference wavetable from the reference set of wavelength calibration parameters for the primary instrument, and step (b) comprises generating an initial target wavetable from the target set of wavelength calibration parameters for the target instrument, each of said wavetables providing a correlation between the pixel locations and the corresponding wavelengths in each respective instrument.

5. A method according to claim 4, further comprising: interpolating the target spectral response measured by the target instrument on to the reference wavetable; and measuring a spectral difference between the target spectral response and the reference spectral response.

6. A method according to claim 5, further comprising: interpolating the spectral difference back to the target wavetable; and subtracting the spectral difference from the initial target spectral response, so as to provide a photometrically corrected target spectral response.

7. A method according to claim 6, further comprising: interpolating the photometrically corrected target spectral response from the initial target wavetable to the reference wavetable to provide a corrected set of measured specral data for the target instrument.

8. A method according to claim 4, further comprising: interpolating both the target spectral response measured by the target instrument and the reference spectral response measured by the reference instrument on to a selected wavetable; and measuring a spectral difference between the target spectral response and the reference spectral response in said selected wavetable.

9. A method according to claim 8, further comprising: interpolating both the spectral difference and the initial target spectral response on to a selected wavetable; and subtracting the spectral difference from the initial target spectral response, so as to provide a photometrically corrected target spectral response.

10. A method according to claim 9, further comprising: interpolating both the photometrically corrected target spectral response and the reference spectral response from the reference table on to a selected wavetable, so as to provide a corrected set of measured spectral data for the target instrument.

11. A method according to claim 7, wherein providing a corrected set of measured spectral data for the target instrument is repeated for each iterative adjustment in step (e).

12. A method according to claim 11, wherein said iterative adjustment comprises step-wise adjusting the pixel locations of the target detector in predetermined steps.

13. A method according to claim 12, wherein step (g) comprises minimizing a parameter representative of spectral residuals of the target instrument, the spectral residuals being the difference between the corrected set of measured spectral data and an estimated set of spectral data for the target instrument.

14. A method according to claim 13, wherein the parameter representative of the spectral residuals is the sum of the absolute values of all residual components across a spectrum of interest.

15. A method according to claim 14, wherein the spectral residuals are calculated, during each iteration, using one of principle components regression, principal components analysis, and partial least squares.

16. A method according to claim 13, wherein the parameter representative of the spectral residuals is one of the mean, median, and root mean square of the absolute values of at least some residual components.

17. A method according to claim 16, wherein the spectral residuals are calculated, during each iteration, using one of principle components regression, principal components analysis, and partial least squares.

18. A method according to claim 4, wherein, said iterative adjustment in step (e) comprises step-wise adjusting the pixel locations of the target detector in predetermined steps.

19. A method of recalibrating the wavelength of a target instrument, said target instrument being provided with a calibration model developed for a primary instrument, the method comprising:

(a) obtaining a reference set of at least two wavelength calibration parameters for the primary instrument;

(b) obtaining a target set of at least two corresponding wavelength calibration parameters for the target instrument;

(c) measuring a reference spectral response of a sample with the primary instrument;

(d) measuring a target spectral response of said sample with the target instrument;

(e) iteratively adjusting the target set of wavelength calibration parameters;

(f) for each target set of wavelength calibration parameters, determining spectral residuals corresponding to that target set; and (g) selecting an optimum set of wavelength calibration parameters based on the spectral residuals for each target set of wavelength calibration parameters.

20. A method according to claim 19, wherein steps (b) and (d) occur after steps (a) and (c), and the target instrument to be recalibrated is the primary instrument.

* * * * *

UNITED STATES PATENT AND TRADEMARK OFFICE
CERTIFICATE OF CORRECTION

PATENT NO. : 6,700,661 B1
DATED : March 2, 2004
INVENTOR(S) : Theodore E. Cadell et al.

It is certified that error appears in the above-identified patent and that said Letters Patent is hereby corrected as shown below:

<u>Title page,</u>
Item [73], Assignee, please delete "CME Telemetrix, Inc" and insert
-- CME Telemetrix Inc. --.

Signed and Sealed this

Sixth Day of September, 2005

JON W. DUDAS
*Director of the United States Patent and Trademark Office*